United States Patent
Oku et al.

(10) Patent No.: US 7,381,419 B2
(45) Date of Patent: Jun. 3, 2008

(54) MEDICAL COMPOSITION KIT FOR TREATING LESIONED ABNORMAL TISSUE

(75) Inventors: Kinuko Oku, Naha (JP); Takako Iwamoto, Tokyo (JP); Takashi Ono, Tokyo (JP)

(73) Assignees: Lequio Pharma Co., Ltd., Okinawa (JP); Mitsubishi Pharma Corporation, Osaka (JP)

( * ) Notice: Subject to any disclaimer, the term of this patent is extended or adjusted under 35 U.S.C. 154(b) by 580 days.

(21) Appl. No.: 10/297,278

(22) PCT Filed: Jun. 5, 2001

(86) PCT No.: PCT/JP01/04720

§ 371 (c)(1), (2), (4) Date: Dec. 31, 2002

(87) PCT Pub. No.: WO01/93856

PCT Pub. Date: Dec. 13, 2001

(65) Prior Publication Data

US 2003/0191070 A1    Oct. 9, 2003

(30) Foreign Application Priority Data

Jun. 6, 2000    (JP) ............................. 2000-168502

(51) Int. Cl.
*A61F 9/02* (2006.01)
(52) U.S. Cl. ...................... 424/434; 424/436
(58) Field of Classification Search ............... 424/434, 424/436; 604/87, 89, 90, 91
See application file for complete search history.

(56) References Cited

U.S. PATENT DOCUMENTS

| | | | | |
|---|---|---|---|---|
| 2,312,715 A * | 3/1943 | Holmes et al. | ............... | 514/23 |
| 2,696,456 A * | 12/1954 | Hetterick | ..................... | 424/436 |
| 2,824,042 A * | 2/1958 | Gibbons et al. | ............ | 514/496 |
| 4,265,883 A | 5/1981 | Cameron | ..................... | 424/154 |
| 4,307,075 A * | 12/1981 | Martin | ..................... | 424/435 |
| 4,395,398 A * | 7/1983 | Yamamoto | ................... | 424/642 |
| 4,797,392 A * | 1/1989 | Chernomorsky | ............ | 514/185 |
| 4,963,591 A * | 10/1990 | Fourman et al. | ............ | 514/781 |
| 5,750,150 A * | 5/1998 | Okazaki et al. | ............. | 424/682 |
| 5,858,371 A * | 1/1999 | Singh et al. | ................ | 424/731 |
| 5,971,953 A * | 10/1999 | Bachynsky | .................. | 604/90 |
| 6,136,337 A * | 10/2000 | Kondo et al. | ............... | 424/436 |
| 6,210,698 B1 * | 4/2001 | Yamazaki et al. | .......... | 424/434 |
| 6,432,415 B1 * | 8/2002 | Osborne et al. | ............ | 424/400 |
| 6,479,058 B1 * | 11/2002 | McCadden | ................... | 424/401 |

FOREIGN PATENT DOCUMENTS

| | | | |
|---|---|---|---|
| CN | 1081880 | * | 2/1994 |
| CN | 1114193 | * | 1/1996 |
| EP | 0 617964 A1 | * | 3/1994 |
| EP | 0 679 401 | * | 11/1994 |
| EP | 0 679401 A1 | * | 1/1995 |
| JP | 7-2680 | | 1/1995 |
| JP | 8-92106 | | 4/1996 |
| JP | 9-143079 | | 6/1997 |
| JP | 9-227383 | | 9/1997 |

OTHER PUBLICATIONS

International Search Report for PCT/JP01/04720.

Z. Shi et al. "Treatment Of Third-Dregree Internal Hemorrhoids With Xiaozhiling Injection A Clinical Investigation On 1205 Cases", Journal of Traditional Chinese Medicine, vol. I, No. 2, 1981, pp. 115-120. (Abstract).

* cited by examiner

*Primary Examiner*—Sharon E. Kennedy
(74) *Attorney, Agent, or Firm*—Kilyk & Bowersox, P.L.L.C.

(57) ABSTRACT

Optimum compounding composition of a local injection preparation for treating rectal submucous lesioned abnormal tissue with local anesthetic is decided to provide a medical composition kit. In a composition kit for the treatment where respective containers are unsealed upon being used and respective contents are mixed to obtain a preparation for injection, a medical composition kit which is characterized in that respective single doses of a therapeutic preparation and local anesthetic are fractionally charged in containers, the said therapeutic preparation contains 1~10% of a water-soluble aluminum compound and 0.01~2% of tannic acid and the said local anesthetic contains 0.1~1% of lidocaine hydrochloride or 0.5~5% of procaine hydrochloride.

18 Claims, 1 Drawing Sheet

MEDICAL COMPOSITION KIT FOR TREATING LESIONED ABNORMAL TISSUE

This application claims the benefit of earlier filed International Application No. PCT/JP01/04720 filed Jun. 5, 2001.

TECHNICAL FIELD

The present invention relates to a medical composition kit for a local injection preparation for treating rectal submucous lesioned abnormal tissue such as hemorrhoid and, more particularly, it relates to a medical composition kit comprising a local injection preparation for treating rectal submucous lesioned abnormal tissue containing a water-soluble aluminum compound and tannic acid and a local anesthetic for treating the same.

BACKGROUND ART

Treatment of internal hemorrhoid by injection has a history of at least 100 years. A ferric sulfate solution or a solution of phenol in olive oil is also one of the earliest known remedies for treating internal hemorrhoids. Other early remedies including alcohol, kinin hydrochloride, mercury chloride, urethane, ergot, etc. had been used. In the recent 30 years, a solution of phenol in vegetable oil or a solution of alum have been mainly used.

Prior compositions for treating internal hemorrhoids do not resolve many problems. For example, in treating hemorrhoid by injection preparations, fibrogenesis of hemorrhoid tissue must end upon termination of bleeding, growth of microbes must be inhibited, no hard nodule should remain and, necrosis should not occur. However, the injection preparations up to now do not satisfy all or most of those demands. Further, in injection preparations used in clinic fields, it is difficult to decide the appropriate concentration and amount of preparation to be administered and also to decide a method for sclerosing the internal hemorrhoid without causing necrosis of the tissue. When the above-mentioned composition is injected, the site where the medicament is concentrated is limited to the submucous tissue only and, therefore, the injected site is to be expanded and the administration method is to be improved as well.

With regard to a composition for the treatment of hemorrhoid, there has been proposed an injection preparation comprising tannin, alum for medical use, sodium citrate, dextran, glycerol and trichlorobutyl alcohol (*Journal of Traditional Chinese Medicine*, 1(2), 115-120 (1981)). Chemical name for alum is aluminum potassium sulfate which is colorless and transparent octahedral crystal and has been known to have local astringent, hemostatic, and antiseptic actions. However, even when this alum is taken per os, it is not absorbed from mucous membranes of stomach and intestine but merely acts locally on the mucous membrane. On the other hand, tannic acid is usually obtained from nutgall or gallnut and is in the form of a yellowish white to pale brown amorphous powder, small leaves, or sponge-like bulk. Tannic acid has been known to coagulate protein in acidic or neutral solution, to show an astringent action, and to have antiseptic and antibacterial actions.

Since the above-mentioned injection preparation uses trichlorobutyl alcohol, there is a probability of causing the following problems. Trichlorobutyl alcohol is a bonded product of carbon with chlorine and produces a radical by absorption of light, to oxidize tannic acid, whereupon tannic acid turns brown or black, and forms a precipitate. When strong energy (such as heat or light) is applied to trichlorobutyl alcohol, chemical bonds in the compound are cleaved, changing the compound into an unstable substance. Because of these properties, it is not appropriate to use trichlorobutyl alcohol for pharmaceuticals, and an injection preparation comprising such a composition has the potential of forming a precipitate during preservation, and consequently requires that preservation should be conducted with utmost care.

In the Japanese Patent Laid-Open No. 04/225,920, there is disclosed a sclerosing agent for lesioned abnormal tissue of digestive organs in which a traditional plant medicine extract containing phenol compound, flavone or flavonoid, catechin compound or polycarboxylic acid is contained as a stabilizer in a composition where aluminum potassium sulfate and tannic acid are compounded as a medicament for sclerosing the lesioned abnormal tissue of digestive organs such as esophageal varix, hemorrhoid, rectal full-thickness prolapse, rectal mucosa prolapse and intestinal or rectal protrude lesioned tissue. However, since an extract of traditional plant medicines is contained in the composition as a stabilizer, it is very difficult to prepare a stabilizer having a predetermined composition and, even after troublesome extracting and purifying steps, there is still a risk that small amounts of unidentified components remain, which is a problem in terms of a pharmaceutical preparation. Further, even when an extract of traditional plant medicines is contained as a stablizer, a composition where aluminum potassium sulfate and tannic acid are compounded may be colored or, in some cases, precipitated when it is preserved for a long period in a state of an aqueous solution and that is a problem as a pharmaceutical preparation for injection.

In WO 94/06443 (International Laid-Open Date: Mar. 31, 1994), there is described an injection preparation for the treatment of lesioned abnormal tissue comprising 0.01~0.5 molar concentration of a water-soluble aluminum compound, 0.5%~25.0% (to the above water-soluble aluminum compound) of tannic acid, sodium hydrogen sulfite and polyhydric alcohol or saccharide having a pH of 1.5~3.5. However, in a method for the manufacture of the composition mentioned in the patent, all constituting components for the composition are just dissolved at the same time or randomly. Thus, the method in this patent for the manufacture of the injection preparation involves placing all components in a test tube, adding water for injection by stirring until a predetermined amount is obtained, placing the resulting aqueous solution in a container such as a glass bottle, removing oxygen dissolved in the solution, filling the container with nitrogen gas, carrying out a high-pressure steam sterilization and preserving the product in a cool place. However, it was found that, in the general method for the manufacture of injection solution in this patent, it is difficult to prepare a composition having a constant composition which is stable in terms of the pharmaceutical preparation. Consequently, it is difficult to manufacture such a composition.

Aluminum potassium sulfate (alum), used as one of the components for the composition of the present invention has been used as a hemostatic agent. It is noted that the Commentary for the Japanese Pharmacopoeia mentions that the use of alum as a pharmaceutical by mixing with tannic acid is prohibited or, in other words, incompatible. However, although it has been attempted, as mentioned already, to mix both alum and tannic acid, for use as a pharmaceutical, coloration results upon mixing, and precipitation is generated, whereby the product is extremely unstable. Use of such an unstable composition as an injection preparation is not adequate and, in addition, unsafe.

Aluminum potassium sulfate usually contains iron which is derived from bauxite. Therefore, in the Japanese Pharmacopoeia, the allowable amount of iron when used as a medical material for aluminum potassium sulfate is regulated to be 20 ppm or less. Further, aluminum potassium sulfate is dissociated in a solution to generate aluminum ions such as $Al^{3+}$, $Al(OH)^{2+}$ and $Al(OH)_2^+$ which react with hydroxyl ion OH to produce aluminum hydroxide $Al(OH)_3$ resulting in precipitate in the solution. When a precipitate is produced in solution as such, the preparation is unsuitable for treatment by injection.

On the other hand, tannic acid is oxidized through contact with oxygen in air or with dissolved oxygen in solution to give oxides, such as quinone compounds, resulting in a precipitate in the injection preparation. When such insoluble products are precipitated in an injection preparation, it goes without saying that such a solution is unsuitable as an injection preparation. Further, air oxidation of tannic acid is promoted to give a precipitate as an oxide especially when iron coexists in the solution. Accordingly, when tannic acid and aluminum potassium sulfate coexist in a solution, iron ions are derived from aluminum potassium sulfate in the solution as mentioned already, whereby the iron ions directly react with tannic acid to form a precipitate and, at the same time, air oxidation is promoted. Furthermore, when aluminum ion exists in solution, tannic acid directly reacts with the aluminum ion to form a precipitate whereby it is apt to be subjected to air oxidation. Accordingly, when the components are merely compounded, it is never possible to manufacture a solution containing tannic acid and aluminum potassium sulfate such that no precipitate is formed and that the composition is constant and is stable.

In order to solve the problems identified above, an injection preparation has already been disclosed, which has a constant and stable composition and which is a composition for treating lesioned abnormal tissue such as hemorrhage by a full consideration of dissolving order, dissolving condition, etc. of the components (Japanese Patent Laid-Open No. 08/92,106).

DISCLOSURE OF THE INVENTION

A local injection preparation for treating rectal submucous lesioned abnormal tissue such as hemorrhoid is usually administered under rectal mucosa. It is believed that administering the local injection under the rectal mucosa causes no sense of pain, although some sense of discomfort can be experienced in the anus or vagus nerve. Therefore, as a means for mitigating the local pain or sense of discomfort in the anus of the patient, the injection is administered jointly with local anesthetic. However, such a use has a possibility of affecting the effectiveness of treatment and the safety of a water-soluble aluminum compound and tannic acid and also has a possibility of incompatibility. Therefore, doses of the water-soluble aluminum compound and tannic acid and selection and dose of local anesthetic are to be determined by taking into consideration the relationship of the combined effect of the drug and of the water-soluble aluminum compound and tannic acid. The present invention provides a local injection preparation for treating rectal submucous lesioned abnormal tissue comprising local anesthetic in an optimum amount.

The present inventors have carried out investigations to determine whether local anesthetic affects the efficacy and safety of water-soluble aluminum compound and tannic acid when a local injection preparation for treating rectal submucous lesioned abnormal tissue containing water-soluble aluminum compound and tannic acid is used together with local anesthetic. For such a purpose, investigations on selection and compounding ratio of use of the local anesthetic were carried out to determine action of incarnation (index for sclerosis of tissue) and drug fate of aluminum. It has been found that local anesthetic can be used jointly without affecting the efficacy of water-soluble aluminum compound and tannic acid by utilizing a very specific amount of local anesthetic. It has been further found that when previously prepared as a medical composition kit, precision of compounding ratio of the anesthetic and the water-soluble aluminum compound and tannic acid can be maintained. Consequently, the problems associated with treatment can be avoided.

Thus, the present invention comprises:

(1) A medical composition kit for treating rectal submucous lesioned abnormal tissue comprising respective containers that can be unsealed upon use to allow contents therein to be mixed to provide a preparation for injection. Respective single doses of a therapeutic preparation and local anesthetic are fractionally charged in the containers, the therapeutic preparation containing 1~10% of a water-soluble aluminum compound and 0.01~2% of tannic acid, and the local anesthetic containing 0.1~1% of lidocaine hydrochloride.

(2) A composition kit for treating rectal submucous lesioned abnormal tissue comprising respective containers that can be unsealed upon use to allow contents therein to be mixed to provide a preparation for injection. Respective single doses of a therapeutic preparation and local anesthetic are fractionally charged in the containers, the therapeutic preparation containing 1~10% of a water-soluble aluminum compound and 0.01~2% of tannic acid and the local anesthetic containing 0.5~5% of procaine hydrochloride.

(3) The medical composition kit for treating rectal submucous lesioned abnormal tissue according to the above-mentioned (1) or (2), wherein the water-soluble aluminum compound, tannic acid and lidocaine hydrochloride or procaine hydrochloride are previously and fractionally charged, yielding a final concentration in the final preparation of 1.5~2.5%, 0.01~0.1% and 0.05~0.5% or 0.1~1%, respectively.

(4) The medical composition kit for treating rectal submucous lesioned abnormal tissue according to the above-mentioned (3), wherein pH of the preparation for the treatment is 2~3.

(5) The medical composition kit for treating rectal submucous lesioned abnormal tissue according to the above-mentioned (3), wherein the water-soluble aluminum compound is aluminum potassium sulfate.

(6) The medical composition kit for treating rectal submucous lesioned abnormal tissue according to the above-mentioned (3), wherein the preparation for the treatment contains a chelating agent and an additive for stabilization.

(7) The medical composition kit for treating rectal submucous lesioned abnormal tissue according to the above-mentioned (6), wherein the concentration in each compound in the final preparation after each component is mixed is 0.5~1% of sodium citrate, 0.1~1% of dextran 40, 3~8% of glycerol and 0.01~0.1% of sodium hydrogen sulfite in addition to water-soluble aluminum compound and tannic acid.

(8) The medical composition kit for treating rectal submucous lesioned abnormal tissue according to the above-mentioned (3), wherein the preparation for local injection and the local anesthetic are each charged in a preservation container under an inert gas atmosphere.

(9) The medical composition kit for treating rectal submucous lesioned abnormal tissue according to the above-mentioned (3), wherein the container of the kit comprises two chambers that are united.

(10) The medical composition kit for treating rectal submucous lesioned abnormal tissue according to the above-mentioned (3), wherein the container of the kit is not permeable to oxygen.

(11) The medical composition kit for treating rectal submucous lesioned abnormal tissue according to the above-mentioned (3), wherein the container of the kit has a two-layered structure comprising outer and inner layers and a deoxidizer is sealed between the inner and outer layers.

(12) The medical composition kit for treating rectal submucous lesioned abnormal tissue according to the above-mentioned (3), wherein the container of the kit is a container for preservation of the preparation for local injection and the local anesthetic.

BEST MODE FOR CARRYING OUT THE INVENTION

Figure 1:
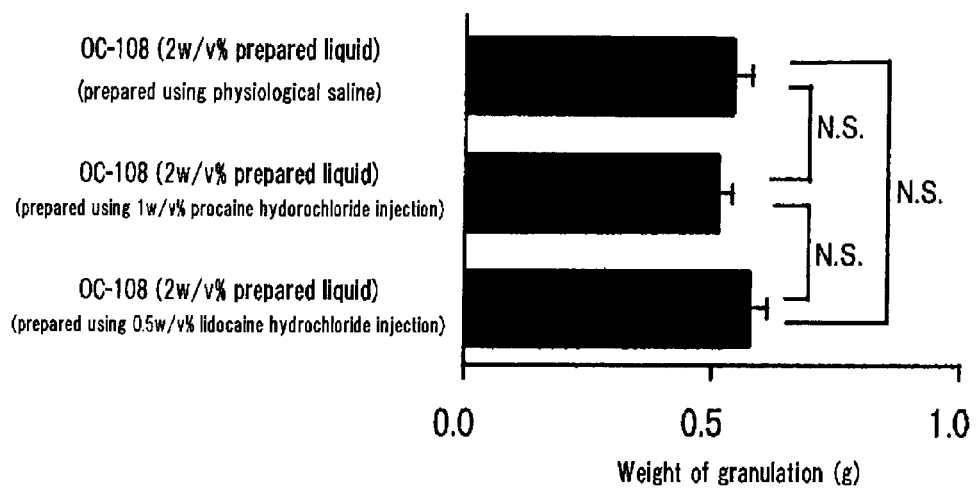
FIG. 1 shows the incarnation action of the medical composition kit of the present invention in terms of weight of granulation. The data shows mean value ±standard error of 8 examples for each group. It should be understood that N. S. stands for "not significant difference".

Examples of the water-soluble aluminum compound in the present invention are aluminum chloride, aluminum sulfate, aluminum carbonate, aluminum acetate, aluminum nitrate, aluminum lactate, aluminum tartrate, aluminum salicylate, aluminum sodium sulfate, aluminum potassium sulfate, aluminum cesium sulfate and aluminum ammonium sulfate. One or more water-soluble aluminum compounds may be used. Particularly preferred of the water-soluble aluminum compounds is aluminum potassium sulfate. It acts by blocking the blood flow of hemorrhoid tissue, whereby hemostatic action is achieved quickly and hemorrhoid is degenerated. In addition, hemorrhoid interstitium tissue is fibrosed via an aseptic inflammation inducing action and mucosa and submucous layer of hemorrhoid (including overextended blood vessel and sustentaculum) are fused and fixed to the muscle layer, whereupon hemorrhoid is sclerosed and degenerated.

It is preferred that the molar concentration of the above-mentioned water-soluble aluminum compound during the fractional charging is 0.01 to 0.5 or, preferably, 0.03 to 0.3 molar concentration. The effective concentration in the fractionally charged preparation is within a range of about 1% to about 10%, preferably about 2% to about 5% or, more preferably, about 4%. The fractionally charged preparation is one of the two components of the medical composition kit of the present invention and its preparation is carried out in such a manner that the final concentration of the water-soluble aluminum compound in the mixed final preparation is about 2%.

With regard to tannic acid that may be used in the present invention, tannic acid that is derived from various plants, etc. may be used, and that derived from gallnut is particularly preferred. The tannic acid does not suppress the tissue sclerosing action of the water-soluble aluminum compound but reduces an excessive acute inflammation reaction which may cause tissue disorder. During the fractional charging, it is compounded together with the water-soluble aluminum compound and its contained ratio in terms of effective concentration in the fractionally charged preparation is within a range of 0.01% to 2%, preferably, 0.0-5% to 1.5% and, more preferably, about 0.15%. The concentration is adjusted in such a manner that the final concentration of tannic acid in the mixed final preparation is about 0.075%. Incidentally, tannic acid may be added in greater amounts than the range provided above, provided that the amount of other components, particularly sodium hydrogensulfite, is adjusted. In that case, however, coloration and precipitation are apt to occur when the prepared composition is preserved for a long term and utmost care is needed for preparation and preservation, which is inconvenient.

In the fractionally charged preparation containing the water-soluble aluminum compound, a chelating agent such as sodium citrate is added so that small amounts of metal ion existing in the solution is trapped and, at the same time, stabilization of the water-soluble aluminum compound is attempted. The amount added in the fractionally charged preparation compared to the amount of the water-soluble aluminum compound is within a range of about 10% to about 80% or, preferably, about 20% to about 50% although that may be appropriately modified depending upon the type, adding amount, etc. of the water-soluble aluminum compound. The preferred adding concentration is about 1.5% and is adjusted so as to make the final concentration 0.75% after mixing. Incidentally, the chelating agent is added to a solution containing the water-soluble aluminum compound before compounding tannic acid with the water-soluble aluminum compound.

In addition, tannic acid is unstable when exposed to light and to air even in its solid state and, therefore, it is believed to be more unstable in a solution in view of diffusion velocity among the reaction substances. Therefore, to prevent the oxidation of tannic acid, an antioxidant such as sodium hydrogen sulfite is added. In the present invention, the contained ratio of sodium hydrogen sulfite used as an antioxidant is usually about 50% to about 200% or, preferably, about 70% to about 150% to tannic acid. The preferred adding concentration in the fractionally charged preparation is about 0.15% and is adjusted so as to make the final concentration about 0.075% after mixing.

In order to further stabilize the fractionally charged preparation containing the water-soluble aluminum compound as such, it is also possible to add to the above composition of necessary polyhydric alcohol and/or saccharide. Examples of such polyhydric alcohol and saccharide are glycerol, glucose, fructose, xylitol, mannose, mannitol, galactose and dextran. Dextran is particularly useful for adjusting the viscosity of the preparation. Such polyhydric alcohol and saccharide may be used solely, or mixed together and used jointly. With regard to the contained rate of such polyhydric alcohol and/or saccharide, although there is no particular limitation provided that the osmotic pressure as compared with a physiological saline is about 3- to about 15-fold or, preferably, about 4- to about 8-fold, it is preferably contained within a range of about 3% to about 20% or, preferably, about 5% to about 15% in terms of an effective concentration in the preparation. Preferred adding concentration in the fractionally charged preparation is about 0.7% of dextran such as dextran 40 and about 10% of glycerol and it is prepared so as to make the final concentrations of dextran and glycerol about 0.35% and about 5%, respectively after mixing.

The fractionally charged preparation containing the water-soluble aluminum compound in accordance with the present invention comprises a composition which is substantially composed of water-soluble aluminum compound, tannic acid, chelating agent and sodium hydrogen sulfite and the pH is adjusted to 1.0~3.5 or, preferably, 2~3. If necessary, pharmacologically nontoxic acid or alkali which is commonly used for the manufacture of the preparation may be used for adjusting the pH of the fractionally charged preparation containing the water-soluble aluminum compound of the present invention to an extent of the above-mentioned range. For the adjustment of the pH as such, it is possible to use a mineral acid such as hydrochloric acid or sulfuric acid, sodium hydrogen carbonate, sodium hydroxide, etc. As a result of controlling the pH of the resulting preparation within the above-mentioned range, the preparation does not result in coloration or precipitation preserved for a long period and is preferably quite stable. A method whereby the above-mentioned pH is maintained even after mixing the preparation for treatment with the local anesthetic is preferred.

Method for the manufacture of the fractionally charged preparation containing a water-soluble aluminum compound in accordance with the present invention is as follows. All components except tannic acid are compounded with sodium hydrogen sulfite in any order and tannic acid is finally compounded therewith. Alternatively a compounded product obtained by compounding a water-soluble aluminum compound with a chelating agent and another compounded product obtained by compounding tannic acid with sodium hydrogen sulfite are separately prepared, those compounds are then mixed and, if necessary, polyhydric alcohol and/or saccharide can be added to at least one of the above compounded products or to a mixture of the compounded products. When the components are compounded as such, oxidation of tannic acid can be prevented and, in addition, direct reaction of tannic acid with metal ion such as aluminum ion derived from aluminum potassium sulfate can be prevented. Consequently, a stable preparation for fractional charge where the composition is constant, containing water-soluble aluminum compound and tannic acid can be prepared.

As a kit constitution, the medical composition kit for treating rectal submucous lesioned abnormal tissue according to the present invention comprises the above-mentioned local injection preparation for treating rectal submucous lesioned abnormal tissue (a fractionally preserved preparation containing a water-soluble aluminum compound) containing a water-soluble aluminum compound and tannic acid, and lidocaine hydrochloride injection or procaine hydrochloride injection as a local anesthetic. Lidocaine hydrochloride and procaine hydrochloride injection are anesthetics which are well known in Japan and they are selected in the present invention due to the reason that they are less likely to cause anaphylaxis as compared with other known local anesthetics. More preferably, lidocaine hydrochloride injection is used. When the influence of the local anesthetic on the incarnation action of the preparation containing the water-soluble aluminum compound and on the fate of the aluminum drug was investigated, both lidocaine hydrochloride injection and procaine hydrochloride injection showed no particular influence. Its concentration in the preparation for fractional charging is 0.1~1% or, preferably, about 0.5% in the case of lidocaine hydrochloride injection.

It is prepared so as to make the concentration 0.05~0.5% or, preferably, about 0.25% after mixing. With regard to lidocaine hydrochloride, lidocaine hydrochloride-epinephrine, lidocaine hydrochloride-epinephrine bitartrate and lidocaine hydrochloride-l-norepinephrine can also be appropriately utilized. In the case of procaine hydrochloride injection, the concentration is 0.5~5% or, preferably, about 1%. It is prepared to make the concentration 0.1~1% or, preferably, about 0.5% after mixing.

Each of the preparations for fractional charging can be included in a kit as a fractionally preserved preparation for each dose for one application and both preparations are used by mixing in actual use. Fractional charging was previously carried out in such a manner that, when both preparations are mixed, the final concentration in the final preparation of water-soluble aluminum compound is about 2%, that of tannic acid is about 0.075% and that of lidocaine hydrochloride or procaine hydrochloride is about 0.25% or about 0.5%, respectively. Each of the preparations for fractional charging is fractionally charged in 2.5~30 mL or, preferably, about 5~20 mL, and both preparations are used by mixing in actual use.

With regard to the container for charging the preparation of each fractionally charged preparation of a medical composition kit for treating rectal submucous lesioned abnormal tissue in accordance with the present invention, a bag, a plastic container, an ampule, a vial or a glass container may be used. The container may be one having an object of mere preservation or may be an injection container for preservation (a pre-filled syringe type). In a method for the manufacture of preparation charged in injection container for preservation, each or any of the components constituting the above-mentioned preparations for fractional charging is manufactured under an atmosphere of inert gas (under such a condition that oxygen in the atmosphere or in the water being used is substantially absent or is only in a limited amount having negative effects on the resulting composition). Nitrogen gas is an example of the inert gas that may be used.

The preparation for fractional charging according to the present invention is charged in a container after conventional aseptic filtration, then subjected to high-pressure steam sterilization if necessary and preserved at room temperature. This charging process is also preferably carried out under the atmosphere of inert gas such as nitrogen gas. Usually, oxygen dissolved in the preparation for injection is deaerated by a conventional method and substituted with nitrogen gas.

The injection preparation which is a fractionally charged preparation according to the present invention can be subjected to freeze-drying in a conventional manner for preparing a kit together with a dissolving agent whereby it is used by dissolving in actual use. With regard to a dissolving liquid for the preparation in actual use, polyhydric alcohol and/or saccharide can be used.

In a medical composition kit for treating rectal submucous lesioned abnormal tissue of the present invention, a charging container for a preparation for local injection containing water-soluble aluminum compound and a local anesthetic can be a two-chamber container having a partition between the two chambers which can be released in actual use to allow mixing, or may be separate containers, and mixing is conducted in actual use although the former is more convenient. A two-chamber container in a united type is commonly used in case the substances which need a fractional preservation are mixed.

Further, it is preferred that the container used for the kit of the present invention is not permeable to oxygen. In addition, it is appropriate for the preservation of the charged preparation to use a container having a two-layered structure comprising outer and inner layers where a deoxidizer is sealed between the inner and outer layers.

The preparation for local injection containing a water-soluble aluminum compound and local anesthetic of the medical composition kit for treating rectal submucous lesioned abnormal tissue according to the present invention are mixed in actual use, and have a fibrosing action administered to sites of digestive organs, particularly the large intestine and rectum, and are able to sclerose and degenerate the lesioned tissue by contacting with lesioned tissue such that suffering from internal hemorrhoid or rectal prolapse and lesioned tissue such as protruded lesioned tissue whereby it is a preparation achieving excellent convenience and certainty in actual use.

EXAMPLES

The present invention will now be illustrated in detail by way of the following Examples and Experimental Examples.

Example 1

Components of the treating preparation and the local anesthetic contained in the kit and their manufacturing methods are as follows.

a. Treating Preparation

Aluminum potassium sulfate (400 mg), 150 mg of sodium citrate, 15 mg of sodium hydrogen sulfite, 15 mg of tannic acid, 70 mg of dextran 40, 1000 mg of glycerol and an appropriate amount of distilled water for injection were used to make the total volume 10 mL. This preparation is called OC-108.

Each component was weighed to give the above compounding and the treating preparation was prepared by the following manufacturing method.

First, water for injection, satisfying the regulation of the Japanese Pharmacopoeia was heated at 100° C. for 5 minutes to remove the dissolved oxygen. After finishing the heating, the water was allowed to cool at room temperature and nitrogen gas was introduced. Since dextran 40 is hardly soluble in water, it was separately and previously dissolved in water for injection completely and the resulting solution was used. After that, sodium hydrogen sulfite was dissolved in an appropriate amount of water for injection, then a dextran 40 solution, sodium citrate, aluminum potassium sulfate and glycerol were added to the resulting solution and, after that, tannic acid was added, whereupon each component was dissolved. During the dissolving step, nitrogen gas was introduced into the solution. The resulting solution was then stirred for about 30 minutes and filtered using a filter. Nitrogen gas was continuously introduced to the filtered solution to give the aimed composition. The pH of this composition was 2.7. Each 10 mL of the composition were charged into a vial or an ampoule. During the charging, pre-substitution and post-substitution with nitrogen gas were carried out and the container was tightly sealed and preserved at room temperature. The resulting liquid was colorless to pale yellow and clear, and slightly viscous. Under an accelerated preservation test condition at 40° C., the liquid was stable for six months. As a result, it was found that the liquid was stable for three years at room temperature. The liquid was stable when exposed to light as well.

b. Local Anesthetic

To lidocaine (Japanese Pharmacopoeia) was added the corresponding amount of hydrochloric acid to prepare a 0.5% lidocaine hydrochloride injection according to the known method for the manufacture of injection preparations, then a preservative such as methyl p-hydroxybenzoate or butyl p-hydroxybenzoate was added thereto and each 10 mL thereof was charged into a vial or an ampoule under the nitrogen gas atmosphere, then sealed tightly.

c. Medical Composition Kit for Treating Rectal Submucous Lesioned Abnormal Tissue There was prepared a medical composition kit for treating rectal submucous lesioned abnormal tissue comprising a fractionally charging preparation containing 10 mL of 0.5% lidocaine hydrochloride injection and a fractionally charging preparation containing 10 mL of local injection solution containing aluminum potassium sulfate.

Example 2

The same operation as in Example 1 was carried out except that 1% procaine hydrochloride injection was used instead of 0.5% lidocaine hydrochloride injection to prepare a medical composition kit for treating rectal submucous lesioned abnormal tissue comprising a fractionally charging preservation preparation containing 10 mL of 1% procaine hydrochloride injection and a fractionally charging preservation preparation containing 10 mL of local injection solution containing aluminum potassium sulfate.

Experimental Example 1

The kit prepared in Example 1 and the kit prepared in Example 2 were used to manufacture each mixed preparation. The amount of the water-soluble aluminum compound in each of the mixed preparations was 2%. As a control, there was prepared a preparation where the amount of the water-soluble aluminum compound was made 2% using a physiological saline (10 mL) instead of the local anesthetic in each kit. An air pouch was formed under the skin of the back of a male rat, the air in the pouch was removed after 2 days, 2 mL of the above-prepared test solution were administered to the site, granulation tissue grown on the pouch site was excised after 14 days from administration and its weight was measured. The result is as shown in FIG. 1 and, in any of the prepared solutions, there was a granulation forming action in the same degree and the influence by the local anesthetic was not noted.

Figure 2:
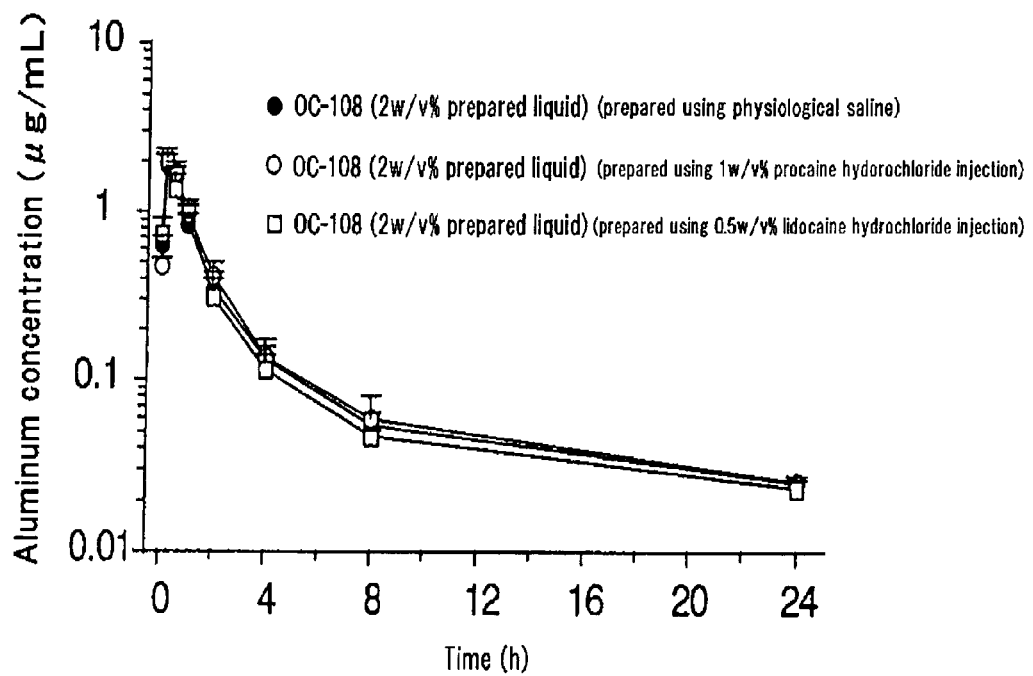
FIG. 2 shows the changes in aluminum concentration in serum after administration of the medical composition kit of the present invention. The data shows mean value ±standard error of 5 examples for each group.

As another experimental system, the same preparation as above was prepared and subcutaneously administered to a male rat in a dose of 20 mg/kg as aluminum potassium sulfate and changes in the concentration of aluminum in serum was measured. Incidentally, the measured value was expressed in terms of aluminum concentration where the value in serum of a rat to which nothing was administered was deducted. The result is as shown in FIG. 2 and any of the prepared solutions showed the same changes in aluminum concentration in serum where there was no significant influence by local anesthetic.

Experimental Example 2

The kit prepared in Example 2 was used and the mixed preparation was directly administered into hemorrhoid of the patients suffering from internal hemorrhoid in a severe state of internal hemorrhoid of degrees III and IV according to the internal hemorrhoid classification by Goligher and fate of the drug, efficacy and safety were investigated. The analyzed cases were 15.

a. EFFICACY

After 28 days from administration, investigations were conducted for degree of improvement in prolapse, bleeding and hemorrhoid size which were the main evaluating items and, as a result, improvements of not lower than medium degree were 100%, 92% and 100%, respectively. No prolapse was noted in all cases and most of hemorrhoid was also sclerosed and degenerated in all cases.

b. SAFETY

With regard to the safety as a whole, "safe" was 80%. As to the side effect, hematuria, pollakisuria and polyuria were noted in one of 15 cases as subjective and objective symptoms. There was no complaint of pain during and after the administration of injection solution, sense of discomfort at anus and uncomfortable feeling at anus in all cases.

c. FATE OF DRUG OF ALUMINUM

Total dose administered to the subject to be analyzed was 27~42 mL and the time for administration was 4~17 minutes. Concentration in serum after administration and excreted rate into urine were expressed by deducting the values before administration in each case. Aluminum concentration in serum before administration was less than the limit for quantification (0.01 µg/mL) in all cases. When 8.4~13.7 mg/kg of aluminum potassium sulfate in the mixed preparation were administered into hemorrhoid, the level reached $C_{max}$ (1.80±0.51 µg/mL) after 0.71±0.37 hour from completion of administration and then, in the final phase, it disappeared with a half-life of 149.3±170.7 hours. $AUC_{0-24h}$ and $AUC_{0-4}$ were 13.8±3.7 and 38.7±14.7 µg/mL, respectively. A dose correlation was noted between the dose (mg/kg) and the values of $C_{max}$ and $AUC_{0-24h}$. Excreted rate of aluminum into urine until 96 hours after the administration was 56.6±11.1%.

d. CONCLUSION

It has been noted from the above that the medical composition kit in accordance with the present invention is a very effective preparation for internal hemorrhoid in a severe degree and that both safety and painlessness are guaranteed.

INDUSTRIAL APPLICABILITY

As illustrated hereinabove, investigations on selection and compounding ratio of use of the local anesthetic were carried out in a preparation of local injection for treating rectal submucous lesioned abnormal tissue containing a water-soluble aluminum compound and tannic acid whereupon it was found that lidocaine hydrochloride or procaine hydrochloride injection, particularly lidocaine hydrochloride injection, was able to be used therewith as a very useful local anesthetic. When previously made into a medical composition kit, the precision of the compounding ratio can be maintained and, in addition, a preparation where safety and painlessness are guaranteed can be provided. Further, the present invention avoids difficulties presented to medical doctors in the therapy and is of much convenience.

The invention claimed is:

1. In a composition kit for the treatment where respective containers are unsealed upon being used and respective contents are mixed to obtain a preparation for injection, a medical composition kit for treating rectal submucous lesioned abnormal tissue comprising respective single doses of a therapeutic preparation and local anesthetic fractionally charged in containers, and said therapeutic preparation contains 1~10% (% wt./vol.) of a water-soluble aluminum compound and 0.01~2% (% wt./vol.) of tannic acid and said local anesthetic contains 0.1~1% (% wt./vol.) of lidocaine hydrochloride or 0.5~5% (% wt./vol.) of procaine hydrochloride.

2. The medical composition kit for treating rectal submucous lesioned abnormal tissue according to claim 1, wherein the water-soluble aluminum compound, tannic acid and lidocaine hydrochloride or procaine hydrochloride are previously and fractionally charged so that the final concentrations of them in the final preparation prepared as an injection preparation by mixing them are made 1.5~2.5%, 0.01~0.1% and 0.05~0.5% or 0.1~1% (% wt./vol.), respectively.

3. The medical composition kit for treating rectal submucous lesioned abnormal tissue according to claim 2, wherein pH of the preparation for the treatment is 2~3.

4. The medical composition kit for treating rectal submucous lesioned abnormal tissue according to claim 2, wherein the water-soluble aluminum compound is aluminum potassium sulfate.

5. The medical composition kit for treating rectal submucous lesioned abnormal tissue according to claim 2, wherein the preparation for the treatment contains a chelating agent and an additive for stabilization.

6. The medical composition kit for treating rectal submucous lesioned abnormal tissue according to claim 5, wherein the final preparation, where each component is mixed to give an injection preparation, is prepared so as to contain 0.5~1% of sodium citrate, 0.1~1% of dextran 40, 3~8% of glycerol and 0.01~0.1% of sodium hydrogen sulfite in addition to water-soluble aluminum compound and tannic acid.

7. The medical composition kit for treating rectal submucous lesioned abnormal tissue according to claim 2, wherein each of the preparation for local injection and the local anesthetic is charged in a preservation container under an inert gas atmosphere.

8. The medical composition kit for treating rectal submucous lesioned abnormal tissue according to claim 2, wherein the container of the kit is a type where two chambers are united.

9. The medical composition kit for treating rectal submucous lesioned abnormal tissue according to claim 2, wherein the container of the kit is not permeable to oxygen.

10. The medical composition kit for treating rectal submucous lesioned abnormal tissue according to claim 2, wherein the container of the kit has a two-layered structure comprising outer and inner layers and a deoxidizer is sealed between the inner and outer layers.

11. The medical composition kit for treating rectal submucous lesioned abnormal tissue according to claim 2, wherein the container of the kit is a container for injection for preservation.

12. The medical composition kit of claim 1, wherein said local anesthetic is 0.5~5% (% wt./vol.) of procaine hydrochloride.

13. The medical composition kit of claim 1, wherein said local anesthetic is 0.1~1% (% wt./vol.) of lidocaine hydrochloride.

14. A mixture comprising 1.5~2.5% (% wt./vol.) water-soluble aluminum compound, 0.01~0.1% (% wt./vol.) tannic acid, and 0.05~1% (% wt./vol.) local anesthetic.

15. The mixture of claim 14, wherein said local anesthetic is lidocaine hydrochloride.

16. The mixture of claim 14, wherein said local anesthetic is procaine hydrochloride.

17. The mixture of claim 14, further comprising a chelating agent, an additive for stabilizing, or both.

18. The mixture of claim 14, wherein said water-soluble aluminum compound is aluminum potassium sulfate.

* * * * *